United States Patent [19]

Miller et al.

[11] Patent Number: 4,507,433

[45] Date of Patent: Mar. 26, 1985

[54] PREPARATION OF OLIGODEOXYRIBONUCLEOSIDE ALKYL OR ARYLPHOSPHONATES

[75] Inventors: Paul S. Miller, Baltimore; Paul O. P. Ts'O, Lutherville, both of Md.

[73] Assignee: The Johns Hopkins University, Baltimore, Md.

[21] Appl. No.: 540,185

[22] Filed: Oct. 7, 1983

[51] Int. Cl.³ .................. C07H 21/02; C07H 21/04
[52] U.S. Cl. .................. 525/54.11; 536/27; 536/28; 536/29
[58] Field of Search ............ 525/54.11, 54.2; 536/27, 28, 29; 424/180

[56] References Cited

U.S. PATENT DOCUMENTS 4,056,673  11/1977  Heimer et al. ............ 424/180

FOREIGN PATENT DOCUMENTS

WO82/03079  9/1982  PCT Int'l Appl.

OTHER PUBLICATIONS

Matteucci et al., "Synthesis of Deoxyoligonucleotides on a Polymer Support", *J. Am. Chem. Soc.*, 1981, v. 103, pp. 3185–3191.

*Primary Examiner*—Morton Foelak
*Assistant Examiner*—Nathan M. Nutter
*Attorney, Agent, or Firm*—Cushman, Darby & Cushman

[57] ABSTRACT

Process for synthesizing deoxyribonucleoside methylphosphonates on polystyrene polymer supports which involves condensing 5'-dimethoxytrityldeoxynucleoside 3'-methylphosphonates. The oligomers are removed from the support and the base protecting groups hydrolyzed by treatment with ethylenediamene in ethanol, which avoids hydrolysis of the methylphosphonate linkages. Two types of oligomers are synthesized: those containing only methylphosphonate linkages, d-Np(Np)$_n$N, and those which terminate with a 5' nucleotide residue, dNp(Np)$_n$N. The latter oligomers can be phosphorylated by polynucleotide kinase, and are separated by polyacrylamide gel electrophoresis according to their chain length. Piperidine randomly cleaves the oligomer methylphosphonate linkages and generates a series of shorter oligomers whose number corresponds to the length of the original oligomer. Apurinic sites introduced by acid treatment spontaneously hydrolyze to give oligomers which terminate with free 3' and 5'-OH groups. These reactions may be used to characterize the oligomers.

15 Claims, 4 Drawing Figures

PREPARATION OF OLIGODEOXYRIBONUCLEOSIDE ALKYL OR ARYLPHOSPHONATES

The work disclosed herein was supported in part by a grant from the National Institute of Health.

The present invention is concerned with certain improvements in the preparation of oligodeoxyribonucleoside alkyl or arylphosphonates.

RELATED APPLICATIONS

Novel and useful oligodeoxyribonucleoside methylphosphonates are described in our U.S. application Ser. No. 206,297, filed Nov. 12, 1980. Further uses of such oligonucleotides are also disclosed in our U.S. application Ser. No. 363,230, filed Mar. 28, 1982. The disclosures of these two applications are incorporated herein by reference.

The instant invention is concerned, inter alia, with improved methods for preparing oligodeoxyribonucleoside alkyl or arylphosphonates, e.g. the methylphosphonates, disclosed in Ser. No. 206,297 and Ser. No. 363,230, and related products.

BACKGROUND OF THE INVENTION

Oligonucleoside methylphosphonates have been used to study the function of specific RNA sequences in biochemical and intact cellular systems. See Miller et al, Biochemistry 20, 1874–1880 (1981) and Jayaraman et al, Proc. Nat'l Acad. Sci. 78, 1537–1541 (1981). Since these nonionic nucleic acid analogs can be taken up intact by mammalian cells and certain bacterial cells in culture, these compounds promise to be useful reagents for exploring and regulating the function of nucleic acids within living cells. See, in this regard, the above-mentioned U.S. applications Ser. No. 206,297 and Ser. No. 363,230.

While various procedures have previously been described for synthesizing oligonucleoside methylphosphonates and the like, there is a real need for a synthesis method which will efficiently and effectively provide oligomers of the desired sequence and length in the yields and amounts required for use.

The synthesis of the methylphosphonate analogs on a silica gel support has previously been described (Miller et al (1983) Nucleic Acids Res.). In that work, protected nucleoside 3'-methylphosphonic chlorides or tetrazolides were used as synthetic intermediates. While oligothymidine methylphosphonates could be efficiently synthesized by this procedure, low yields were encountered when other nucleosides, particularly d-[(MeO)$_2$Tr]ibuG, were used. Recently the preparation of oligonucleoside methylphosphonates on a glass support using nucleoside 3'-methylphosphine chlorides as reactive intermediates has been described (Sinha et al, Tetrahedron Letters, 24, 877–880, 1983). However, there continues to be a need for an efficient and convenient method for synthesizing oligonucleoside methylphosphonates of a desired sequence.

OBJECTS OF THE INVENTION

The principal object of the present invention is to obviate or minimize previous synthesis problems and provide an improved and efficient method for synthesizing oligodeoxyribonucleoside alkyl or arylphosphonates, notably methylphosphonates, of preselected sequence and length in high yield. Other more specific objects will also be hereinafter apparent.

BRIEF DESCRIPTION OF THE INVENTION

Broadly stated, the objects of the invention are realized, at least in part, by the provision of a synthesis method which comprises condensing (1) a 5'- protected nucleoside 3'- alkyl or arylphosphonate with (2) a nucleoside or oligomer thereof bound to a solid or insoluble polymer support, e.g. a polystyrene support. The condensation can be repeated as many times as necessary, with the same nucleoside (1) or a different one, to ultimately obtain an oligonucleoside phosphonate having the desired sequence and length. Typically the invention may be used to prepare an oligomer containing up to nine nucleoside units or even more.

The invention also provides convenient means for removing base protecting groups and for separating the final oligonucleoside product from the polymer bound thereto. Additionally the invention includes means for cleaving the oligonucleoside phosphonate product at apurinic sites to obtain individual nucleoside components or shorter length oligomers of the analog subjected to cleavage. This is useful in confirming the sequence of the product.

DETAILED DESCRIPTION

The invention is hereinafter described by reference to the synthesis of deoxyribonucleoside methylphosphonates by condensing a 5'-dimethoxytrityldeoxyribonucleoside 3'-methylphosphonate alkylamine salt with a deoxynucleoside bound via the 3'- position to a polystyrene support. The dimethoxytrityl (DMTr) groups serves to protect the 5'-hydroxy groups. Other protecting groups (e.g. benzoyl or isobutyl) are used to protect the base portion of the nucleoside throughout the process for preparing the desired product. However, it will be recognized that other protecting groups than dimethoxytrityl and the indicated base protecting groups may be used. Other modifications will also be evident to those in the art.

The invention contemplates the use of any polymer support which is insoluble in the reaction medium and to which the nucleoside can be removably linked. Polystyrene is the preferred support, particularly if it includes a degree of cross-linking, for example, in the order of 1–5% by weight.

According to another preferred aspect of the invention, the final oligomer product which results from the indicated condensation or repetitions thereof to obtain the desired length and sequence, is separated from the polymer support simultaneously with the removal of the base protecting groups by treatment with a diamine alkane containing, for example, up to six carbons. Representative diaminoalkanes include 1,3-diamino propane and 1,4-diamino butane dissolved in a suitable solvent. Preferably, however the diamino alkane is ethylenediamine dissolved in ethanol or the equivalent. It has been found that this treatment is effective for both separation from the polymer and removal of base protecting groups while avoiding hydrolysis of the methylphosphonate linkages.

A unique advantage of the present process is that the condensation cycle, separation from the support and removal of base protecting groups and purification can be carried out in the same vessel thus obviating the need for transferring the product from one vessel to another for processing.

The examples which follow illustrate the synthesis of two types of oligomers, namely, those containing only methylphosphonate linkages, d-Np(Np)$_n$N, and those which terminate wit a 5' nucleotide residue dNp(Np)$_n$N. According to the invention an advantage of the latter oligomers is that they can be phosphorylated by polynucleotide kinase, and may be separated by polyacrylamide gel electrophoresis according to their chain length. This is useful in characterizing the product.

It has also been found that piperidine randomly cleaves the oligomer methylphosphonate linkages and generates a series of shorter oligomers whose number corresponds to the length of the original oligomer. Additionally, apurinic sites introduced by acid treatment spontaneously hydrolzye to give oligomers which terminate with free 3' and 5' OH groups. These reactions may also be advantageously used to confirm sequence and structure and to otherwise characterize the oligomers.

One preferred way of practicing the present invention is illustrated in FIG. 1. The process there exemplified comprises (a) removing the protecting group (DMTr) on a nucleoside or oligonucleoside bound to crosslinked or cross-linkable polystyrene (S) to provide the polymer bound reactant (I); and (b) condensing reactant (I) through its now deprotected 5'- OH group with a 5'-protected nucleoside methylphosphonate alkylamine (II) to obtain the desired oligodeoxynucleoside product (III). The reference letters B and B' represent simplified designations of protected pyrimidine or purine bases as conventional in DNA nucleosides. As is known in the art, each DNA nucleoside is composed of a purine or pyrimidine base joined to deoxyribose sugar. The DNA bases include adenine, guanine, cytosine and thymine which are generally represented by the letters A, G, C and T, respectively. The first two of these are purine bases while the last two (C and T) are pyrimidine bases.

In using the present invention, the reactant nucleosides will be selected to provide the desired base sequence in the oligonucleotide product, it being understood that condensation between product (III) and a nucleoside (II), with appropriate choice of bases (B) and (B'), may be repeated a number of times to give a final product (III') having the desired oligomer length and sequence. As noted earlier, oligomers comprising up to nine, and even more, nucleoside methylphosphonate units may be prepared in this way.

According to the process shown in FIG. 1, the 5'-DMTr protected nucleoside is bound via its 3'- position to an aminomethyl succinyl-derivatized polystyrene support. The 5'- protecting group is removed by using, for example, 1 M zinc bromide solution. The deprotected nucleoside is then condensed with a DMTr protected nucleoside 3'-methylphosphonate trialkyl ammonium salt, specifically the triethyl ammonium salt although other generally equivalent salts may be used. The condensation, as shown in FIG. 1, is carried out with mesitylenesulfonyl-3-nitrotriazole (MSNT) in the presence of acetic anhydride although it will be appreciated that other condensing agents may also be used provided these agents and the other conditions used do not cause undesired side reactions, e.g. hydrolysis, deprotection of the unsupported nucleoside reactant, etc.

Table I below lists oligomers which have been synthesized on polystyrene supports using the process described in Example 1 and FIG. 1 except as otherwise stated:

TABLE I

| | Protected oligomer (a) | Support crosslinking (%) | Average Yield per Coupling step (b) (%) |
|---|---|---|---|
| 1 | d-[(MeO)$_2$Tr]bzCpbzApT—S | 1 | 81 |
| 2 | d-[(MeO)$_2$Tr]ibuGpbzCpbzCpbzApT—S | 1 | 82 |
| 3 | d-[(MeO)$_2$Tr]bzCpbzApibuGpibuGpTpbzApbzA—S | 2 | 83 |
| 4 | d-[(MeO)$_2$Tr]bzCpTpTpbzApbzCpbzCpTpibuG—S | 2 | 85 |
| 5 | d-[(MeO)$_2$Tr]TpbzCpbzCpTpbzCpbzCpTpibuG—S | 2 | 86 |
| 6 | d-[(MeO)$_2$Tr]TpTpTpbzApbzCpbzCpTpT—S | 1 | 83 |
| 7 | d-[(MeO)$_2$Tr]bzApbzApbzA—S | 1 | 83 |
| 8 | d-[(MeO)$_2$Tr]bzApbzCpbzCpbzApT—S | 1 | 81 |
| 9 | d-[(MeO)$_2$Tr]bzApibuGpbzCpbzApbzApibuG—S | 2 | 74 |
| 10 | d-[(MeO)$_2$Tr]bzApbzApbzApbzApibuGpbzCpbzApibuG—S | 1 | 86 |

(a) p = methylphosphonate linkages
p = p-chlorophenyl phosphotriester linkage
S = polystyrene support
(b) Determined by analysis of the dimethoxytrityl group after each coupling step.

The invention is illustrated, but not limited, by the following examples:

EXAMPLE 1

Except as otherwise stated, the protected oligonucleoside methylphosphonate listed in Table I were prepared as follows:

The synthesis was carried out in a polypropylene column fitted with a Teflon 3-way valve and a rubber septum cap. During washing operations, the septum cap was removed and the 3-way valve was connected to a filter flask via a Luerer adaptor and tubing set. Generally vacuum was not required to wash the support. During the drying step, one port of the 3-way valve was connected to a cold trap and vacuum pump via the barrel of a 1 ml plastic syringes. The other port was connected to a Drierite column filled with dry argon.

The reaction cycle which was used consisted of the following steps:

(1) The polystyrene support (60 mg, 1% crosslinked) in the column was washed with three 2 ml portions of methylene chloride/isopropanol (85:15, v/v).

(2) The support was then treated with 2 ml of 1 M zinc bromide in methylene chloride/isopropanol solution. Two five-minute treatments were used when the support-bound nucleoside was d-[(MeO)$_2$Tr]bzA or d-[(MeO)$_2$Tr]ibuG, while four treatments were used when the nucleoside was d-[(MeO)$_2$Tr]T or d-[(MeO)$_2$Tr]bzC. After each treatment the orange solution was collected in a clean flask.

(3) The support was then washed with two ml portions of methyl chloride/isopropanol and the washings were collected in same flask used in step (2). The solution was diluted to 50 ml and a 0.20 ml aliquot was dissolved in 0.80 ml of perchloric acid/ethanol (3:2, v/v). The absorbance was determined at 500 nm and the amount of trityl cation was determined using a molar extinction coefficient of 89,000.

(4) The column was attached to a waste flask and the support was washed with three 2 ml portions of 0.5 M triethylammonium acetate in dimethylformamide; three 2 ml portions of anhydrous pyridine and three 2 ml portions of diethyl ether.

(5) The column was fitted with the septum cap and set up in the drying mode under house vacuum for at least 5 min.

(6) The support was dried by adding 300 1 of anhydrous pyridine via a gas tight syringe. After the support had swollen, the vacuum (oil pump) was applied and the support was warmed with a stream of air from a hair dryer. Evaporation was continued for 10 min. Dry argon was then admitted and the drying operation was repeated two more times.

(7) The coupling mixture was prepared by dissolving 0.20 mol of MSNT in 320 1 of anhydrous pyridine. The solution was then transferred to the vial containing 0.06 mmol of d-[(MeO)$_2$Tr]Np.Et$_3$NH. The nucleotide was dissolved by vortexing and the coupling solution was then added dropwise to the support. It was deemed important to add the solution slowly and to allow the support to swell. Trapped gas bubbles could be removed by gently tapping the column. The entire operation was carried out using one predried syringe. The syringe was left in the V-vial while the reagents were being dissolved.

(8) The reaction mixture was kept at room temperature (22° C.) for two hours.

(9) The column was set up in the washing mode and the support was washed with three 2 ml portions of anhydrous pyridine. The solution, which contained unreacted nucleoside 3'-methylphosphonate and MSNT, was collected in a separate flask. A 50% aqueous pyridine solution (1 ml) was added and the solution was kept at 4° C. for later purification and recovery of d-[(MeO)$_2$Tr]Np.

(10) The support was treated with a solution containing 2 ml of anhydrous pyridine, 1 ml of acetic anhydride and 20 mg of dimethylaminopyridine for 30 min.

(11) The process was then repeated as necessary beginning with step (1) in order to obtain the oligomer products listed in Table I.

Oligomers 7, 8 and 10 (Table I) were synthesized as described above with the exception that step (10) was not used for oligomer 10. The other oligomers of Table I were synthesized in essentially the same manner except the condensation reactions were run in 1 ml V-vials or in glass reaction columns. When the reactions were run in V-vials, the support was dried by several evaporations with anhydrous pyridine in the V-vial. When the reactions were run in the glass reaction column, the support was dried by a single evaporation with anhydrous pyridine overnight at room temperature.

EXAMPLE 2

This example illustrates the methods found to be the most effective for cleaving the oligonucleotide product from the 1% crosslinked support and for removing the base protecting group with minimal hydrolysis of the phosphonate backbone.

The following steps were used for deprotecting oligomers 7, 8 and 10 (Table I):

(1) After the final condensation step the support (60 mg) was washed with three 2 ml portions of anhydrous pyridine; three 2 ml portions of methylene chloride/isopropanol and three 2 ml portions of diethyl ether. The support was then dried under house vacuum.

(2) The support was then swollen by addition of 2 ml of pyridine and the excess was removed under house vacuum.

(3) The support was treated with 3 ml of 0.017 M tetra-n-butylammonium fluoride in tetrahydrofuran/pyridine/water (8:1:1, v/v) for 40 hours at room temperature (20°–25° C.). No shaking was required. The support was then washed with three 2 ml portions of 50% pyridine/water; three 2 ml portions of pyridine; and three 2 ml portions of methylene chloride/isopropanol.

(4) The support was thereafter treated with 3 ml of ethylenediamine/ethanol (1:1, v/v) for 7 hours at room temperature without shaking. The solution was collected and the support was washed with four 2 ml portions of pyridine/ethanol (1:1, v/v) and four 2 ml portions of N,N-dimethylformamide. The combined eluate and washings were evaporated at 25° C. and the oily residue was coevaporated several times with 50% aqueous ethanol. The resulting product was the oligonucleoside separated or cleaved from the support and with the base protecting group removed. Basically this required treatment of the supported oligomer with ethylenediamine/ethanol mixture and washing of the support with anhydrous pyridine.

Oligomer 9 was deprotected in a similar fashion to that set forth above except that step (4) was carried out at 65° C. for 3 hours. For oligomers 1–6, step (3) was not included and step (4) was carried out at 65° for 3 hours.

In each instance, effective separation from the support and deprotection without any undesired effect on the phosphonate linkage or other portions of the nucleoside, were obtained.

The composition of the ethylene diamine/ethanol mixture can be varied (for example, 1–5 parts by volume of diamine can be used per part of ethanol) although a 1:1 mixture has been found particularly effective.

The temperature of the cleavage and deprotecting treatment can also be varied although it is generally adequate to operate at room temperature (20°–25° C.). If necessary or desirable, higher temperature (e.g. up to 100° C.) can be used although, in any case, care should be taken to avoid temperatures which will cause undesired side reaction, e.g. hydrolysis or the like effecting the phosphonate linkages.

EXAMPLE 3

This example describes the purification of the separated oligonucleoside methylphosphonates obtained in the manner described in Example 2.

For oligomers which contain only methylphosphonate linkages (1–6), the residue from step (4) of Example 2 was dissolved in a small volume of 50% aqueous ethanol. The solution was chromatographed on a C-18 reversed phase column (0.46 cm×25 cm for 100 $A_{254}$ units or less; 0.9 cm×50 cm for more than 100 $A_{154}$ units) using a linear gradient of 0% to 25% (8-mer or less) or 0% to 35% (9 mer) acetonitrile in water to remove non-tritylated oligomers. The desired tritylated oligomer was eluted with 50% acetonitrile in water. The solvents were evaporated and the residue was treated with 1 ml of 80% acetic acid in water for 1 hr at room temperature. The solvents were evaporated and the residue was repeatedly evaporated with ethanol to ensure complete removal of acetic acid. The oligomer was then purified by C-18 reversed phase HPLC using a 0% to 25% or 30% acetonitrile in water gradient.

For oligomers which terminate with a 5'-nucleoside phosphodiester linkage (7-10) the residue from step 4) described in Example 2 was treated with 80% acetic acid in water for 15 min. at room temperature. After removal of the acetic acid by evaporation, the residue was dissolved in 20 ml of 50% aqueous ethanol and the solution was passed through a DEAE cellulose column (2.5×8 cm, bicarbonate form) which had been previously washed with 50% aqueous ethanol. The column was monitored at 254 nm and washed with 50% aqueous ethanol until the pen returns to the baseline. The desired oligomer was then eluted with 0.15 M triethylammonium bicarbonate in 50% aqueous ethanol. The buffer was removed by evaporation and coevaporated with 50% aqueous ethanol. The oligomer was then further purified by C-18 reversed phase HPLC using a 0% to 30% acetonitrile in 0.10 M ammonium acetate (pH 5.8) gradient. The oligomer was freed of ammonium acetate by desalting on a Bio-Gel P-2 column (1.5×20 cm).

As will be evident, this example (Example 3) illustrates two methods for purifying oligomers following cleavage from the support. For oligomers which contain only methylphosphonate linkages, the tritylated oligomer was isolated by preparative reversed phase HPLC. This separation is based upon the greater affinity of the tritylated oligomer for the hydrophobic C-18 matrix of the column. Shorter, non-tritylated oligomers were first eluted with a 0% to 25% or 0% to 35% acetonitrile in water gradient. The tritylated product was then eluted with a step gradient of 50% acetonitrile in water.

The dimethoxytrityl group was removed from the material in the 50% acetonitrile fraction by treatment with 80% acetic acid at room temperature. Because these oligomers were originally cleaved from the support by ethylenediamine/ethanol (1:1, v/v) at 65° C., it was usually found that the tritylated oligomer fraction contained shorter oligomers in addition to the desired product. These were easily separated by preparative reversed phase HPLC. While this purification procedure is qualitatively satisfactory, recoveries from the reversed phase columns varied from 50% to 90%. These losses which appeared to be due to irreversible absorption of the oligomers to the column varied depending on the base composition of the oligomers.

For the oligomers which terminate with a 5'- nucleoside phosphotriester group, the support was first treated for 40 hrs with tetra-n-butylammonium fluoride to remove the p-chlorophenyl protecting group. These oligomers were then cleaved from the support and the base protecting groups were removed by treatment with ethylenediamine/ethanol (1:1, v/v) for 7 hrs at room temperature. For example, the reversed phase HPLC profile for products obtained after cleavage of the nonamer, d-[(MeO)$_2$Tr]ApApApApGpCpApApG, is shown in FIG. 2a. The peaks marked with (X) are from impurities in the solvents used to elute the oligomer from the support. The tritylated nonamer appears at 22 min in the chromatogram and is eluted with 50% aqueous acetonitrile. After removal of the dimethoxytrityl group, the nonamer elutes at 15.2 min (FIG. 2b). The peaks which appear between 19 and 25 min are shorter oligomers which contain a 5'-mesitylenesulfonate group.

At this stage, the nonamer was partially purified by ion exchange chromatography on the DEAE cellulose column. This step, which resulted in 84% recovery of material loaded onto the column, removed most of the shorter oligomers as shown in FIG. 2c. After removal of the buffer, the nonamer was purified by preparative reversed phase NPLC using a 0% to 30% acetronitrile in 0.1 M ammonium acetate gradient. The recovery of material from the column (84%) appears to be higher when ammonium acetate is used. The pure nonamer (FIG. 2d) was obtained in 10% overall yield based on the amount of d-[(MeO)$_2$Tr]ibuG originally bound to the polystyrene support. The oligomer was desalted on a Bio-Gel P-2 gel filtration column. Similar results were obtained for the other oligomers purified by this method. Thus, for example, dApApA and d-ApCpCpApT were obtained in 44% and 22% isolated yields respectively based upon the amount of d-[(MeO)$_2$Tr]N.

EXAMPLE 4

Oligomers which terminate with a 5'-nucleotide phosphodiester may be treated with spleen phosphodiesterase to give the oligonucleoside methylphosphonate as follows:

The oligomer (3 $A_{254}$ units) is dissolved in 40 μl of water and treated at 37° C. for 2 hrs with 10 μl (1-2 units) of spleen phosphodiesterase dissolved in water. The completeness of the reaction is determined by reversed phase HPLC. The solution is then diluted with 50 μl of water and passed through a DEAE cellulose column (0.5×1 cm). The column is washed with 500 μl of water and the oligomer is recovered by lyophilization.

EXAMPLE 5

This example describes the recovery of protected nucleoside 3'-methylphosphonate from the reaction mixture of Example 1.

The aqueous pyridine solution from step (9) of Example 1 was evaporated after addition of 0.1 ml of triethylamine. The residue was dissolved in 50 ml of chloroform and the solution was extracted twice with 50 ml of 1 M ammonium bicarbonate. The chloroform layer was dried over anhydrous sodium sulfate. Several drops of triethylamine were added to clarify the solution. After filtration the solvents were evaporated and the residue was evaporated with three 2 ml portions of anhydrous pyridine on an oil pump. The foamy residue was dissolved in 2 ml of dry methylene chloride and the solution was added dropwise to a stirred solution of 1% triethylamine in hexane. The resulting precipitate was collected via filtration on a sintered glass filter, washed with hexane and dried in a vacuum desiccator. The product thus recovered was the protected nucleoside 3'-methylphosphonate, d-[(MeO)$_2$Tr]Nlp.

EXAMPLE 6

This example describes the removal of base protecting groups, specifically benzoyl (bz) and isobutryl (ibu), from nucleosides by using ethylene diamine, specifically ethylene diamine in ethanol.

Several mg of d-[(MeO)$_2$Tr]bzA, d-[(MeO)$_2$Tr]bzC and d-[(MeO)$_2$Tr]ibuG were each dissolved in 250 μl of ethylenediamine/ethanol (1:1, v/v). The solutions were incubated at room temperature. At various times aliquots were chromatographed on silica gel TLC plates which were eluted with 10% methanol in chloroform. The spots corresponding to the starting material and the product were cut out and treated with 1.5 ml of perchloric acid/ethanol (3:2, v/v)1 for 30 min. The absorbance of each solution was measured at 500 nm and the percent reaction was determined. The half-lives of the reactions, in terms of the time required to remove 50% of the base protecting group (DMTr) are given in Table II.

TABLE II

| Protected Nucleoside | Times required to remove 50% of the base protecting groups (min) | Times required to cleave 50% of the nucleoside from the 1% crosslinked support (min) |
|---|---|---|
| d-[(MeO)$_2$Tr]bzA | 10 | 105 |
| d-[(MeO)$_2$Tr]bzC | 20 | 105 |
| d-[(MeO)$_2$Tr]ibuG | 40 | 54 |
| d-[(MeO)$_2$Tr]T | — | 105 |

The above results show that ethylenediamine may be effectively used to remove the base protecting groups (bz and ibu). It is an important feature of the invention that this removal with a base may be accomplished without cleaving or otherwise undesirably effecting methylphosphonate linkages.

EXAMPLE 7

This example illustrates the removal of protected nucleosides from polystyrene supports.

Five mg of d-[(MeO)$_2$Tr]TS (1% crosslinked), d-[(MeO)$_2$Tr]bzAS (1% crosslinked), d-[(MeO)$_2$Tr]bzCS (1% and 2% crosslinked) and d-[(MeO)$_2$Tr]ibuGS (1% and 2% crosslinked), where S represents the polystyrene support, were each treated with 500 μl of ethylenediamine/ethanol (1:1, v/v) solution at room temperature. At various times, 10 μl aliquots were removed, the solvent was evaporated and the residue was dissolved in 1 ml of perchloric acid/ethanol solution (3:2, v/v). The amount of dimethoxytrityl cation and hence the amount of nucleoside cleaved from the support was determined by measuring the absorbance at 500 nm. The half lives for cleavage of protected nucleosides from the 1% crosslinked support are given in Table II.

As shown in Table II, the deoxyguanosine nucleoside was cleaved most rapidly while the other three nucleosides had essentially the same rates of hydrolysis. All the nucleosides are completely removed from the support within 7 hrs. In contrast, very different rates were observed for the 2% cross-linked supports. In these cases, very little cleavage occurred during the first 4 hrs of incubation after which increasing amounts of nucleoside were released over a 24 hr period. This effect may have been due to the slower swelling rate of the 2% crosslinked support versus the 1% support. The results of these experiments indicate that, although condensation reactions occur with equal efficiencies on both the 1% and 2% crosslinked supports, the 1% support is preferred for synthesis since the oligomer can be removed more readily under mild conditions.

EXAMPLE 8

The stability of the methylphosphonate linkage in a number of oligomers of varying chain length and base composition was examined by measuring the degree of hydrolysis of the methylphosphonate linkage following prolonged exposure to ethylenediamine/ethanol at room temperature. This was accomplished as follows:

Oligonucleoside methylphosphonates (1.25 A$_{254}$ units each) were treated with 50 μl of ethylenediamine/ethanol (1:1, v/v) at room temperature (22° C.). Aliquots (10μl) were withdrawn at various times and the solvents were evaporated. The residue was dissolved in 20 μl of 50% aqueous ethanol and the solution examined by C-18 reversed phase HPLC using a 0% to 25% acetonitrile in water gradient. The mole percent of starting oligomer remaining after 100 hrs of treatment is given in Table III.

TABLE III

Hydrolysis of Oligonucleoside Methylphosphonates by Ethylenediamine at 22° C.

| Oligomer | Mole percent of oligomer remaining after treatment for | | |
|---|---|---|---|
| | 24 hrs | 48 hrs | 96 hrs |
| d-TpA | 100 | 100 | 100 |
| d-ApT | 100 | 100 | 100 |
| d-TpT | 100 | 100 | 100 |
| d-TpTpT | 95 | 97 | 91 |
| d-GpGpT | 100 | 100 | 100 |
| d-ApApA | 93 | 87 | 75 |
| d-CpCpApT | 92 | 83 | 67 |

As shown in Table III, some of the oligomers, most notably the dimer and d-GpGpT, were completely stable over a 96 hr period. The maximum rate of hydrolysis for a methylphosphonate linkage in those oligomers which were hydrolyzed is estimated to be 0.13 mole %/hr. The results of these studies show that the oligonucleoside methylphosphonates can be cleaved from the 1% crosslinked support and completely freed of base protecting groups with little or no hydrolysis of the methylphosphonate linkage by treatment with ethylendiamine/ethanol (1:1, v/v) at room temperature for 7 hrs. These conditions can, therefore, be used for cleavage from the support and for removal of base protecting groups.

EXAMPLE 9

This test was used to determine hydrolysis of the oligonucleoside methylphosphonate linkage in acid. Six A$_{254}$ units of oligomer were dissolved in 100 1 of 0.01 M hydrochloric acid solution. The solution was heated at either 45° or 65° C. Aliquots (10 1) were withdrawn at various times and added to 10 1 of 0.015 M ammonium hydroxide at 0° C. The samples were then injected directly onto a C-18 reversed phase column which was eluted with 50 ml of a linear gradient of 0% to 25% acetonitrile in water at a flow rate of 2.5 ml/min. The products of the reaction was determined by comparison with authentic samples.

EXAMPLE 10

The 5' end of oligonucleoside methylphosphonates was labelled with T4-polynucleotide kinase as follows:

Oligonucleoside methylphosphonate (2 nmol) were dissolved in a buffer solution containing 50 mM Tris-HCl (pH 9.0), 10 mM MgCl$_2$, 5 mM dithiothreitol, 20 μM spermidine, and [μ-$^{32}$p]ATP (8 Ci, 4 Ci/mmol). T4-polynucleotide kinase (4 units) was added to the solution, which was made up to 50 μ ml by adding water. The solutions were incubated at 37° C. for 2 hrs. The reaction was checked by PEI-cellulose TLC. The PEI-cellulose plate (2×20 cm, Merck) was preactivated by elution with 1.2 M pyridinim formate (pH 0.5). Small aliquots (0.1 μl) of PNK reaction solutions were applied and developed with 1.5 M pyridinium formate (pH 3.5). The TLC plate was dried and autoradiographed using an intensifying screen at room temperature.

EXAMPLE 11

Gel-electrophoresis of 5' labelled oligonucleoside methylphosphonates as obtained in Example 10 was carried out as follows.

Polyacrylamide gels were prepared by polymerizing a solution containing 18% (v/v) acrylamide, 0.8% (w/v), N,N'-methylenebisacrylamide. 7 M urea, 89 mM tris-borate (pH 8.2), 2 mM EDTA, 0.07% (w/v) ammonium persulfate, in the presence of N,N,N',N'-tetramethylethylenediamine (20μl/20 ml solution). The solution was poured into a 0.75×140×150 mm mold and allowed to polymerize for 2 hrs at room temperature. 5'-labelled oligonucleoside methylphosphonates were dissolved in 10% aqueous glycerol solution containing 0.04% bromophenol and applied to the gel. The electrophoresis was run using 89 mM trisborate buffer containing 10 mM EDTA. After electrophoresis the gel was dried using a gel-dryer and autoradiographed using intensifying screens at room temperature.

EXAMPLE 12

Partial cleavage of oligonucleoside methylphosphonates with hydrochloric acid or piperidine was carried out as follows.

Aliquots (1 μl) from the polynucleotide kinase reaction mixture were incubated with 1 μl of 1 M hydrochloric acid at 37° C. for 30 min. After incubation the solution was neutralized with 1 μl of 1 M ammonium hydroxide and then allowed to stand at room temperature for 10 min before cooling to 0°. Alternatively, aliquots (1 1) from the phosphorylation reaction were incubated with 1 μl of 1 M aqueous piperidine at 37° C. for 10 min after which the solution was cooled to 0° and evaporated. The treated samples were then subjected to polyacrylamide gel electrophoresis as described above without further purification.

The experimental work referred to above can be summarized as follows:

Table I shows representative protected oligonucleoside methylphosphonates which have been synthesized on aminomethyl succinyl-derivatized polystyrene supports according to the invention. The basic synthetic steps which are shown in FIG. 1 are described in detail in Example 1. These steps are: (1) removal of the dimethoxytrityl group with 1 M zinc bromide solution; (2) drying the support in a co-evaporation with anhydrous pyridine; (3) reaction of the support-bound nucleoside or oligonucleotide with a coupling mixture containing 0.15 to 0.2 M d-[(MeO)$_2$Tr]-Np.Et$_3$NH and 0.3 to 0.6 M mesitylenesulfonyl-3-nitrotriazole in anhydrous pyridine and (4) acetylation of unreacted 5'-OH groups with acetic anhydride. The reactions and washing steps were most conveniently carried out in a polypropylene Econo Column fitted with a septum cap and a 3-way Teflon stopcock. Thus no transfers of the support are required using this apparatus.

The synthetic procedure illustrated above is analogous to the phosphotriester approach used to prepare protected oligonucleotide phosphotriesters on polystyrene supports.

However, it has been found that the methylphosphonate coupling reaction is extremely sensitive to moisture. Thus drying procedures such as washing with anhydrous solvent or blowing dry nitrogen gas through the support which are satisfactory for phosphotriester synthesis result in low yields of the methylphosphonates. According to the invention, the best yields are obtained when the support is co-evaporated with anhydrous pyridine by directly attaching the reaction column to a vacuum pump and dry-ice trap. Three 10 min co-evaporations were sufficient to render the support anhydrous.

The protected nucleoside 3'-methylphosphonate triethylammonium salts used in the coupling reactions were prepared from their cyanoethyl ester derivatives in known manner. These monomers were recovered after each coupling step and were freed of unreacted MSNT by a simple extraction step. After precipitation and drying, the monomers could be reused for other syntheses. The ability to recover the unreacted monomers is particularly important for large scale synthesis since large excesses of these materials are employed in the coupling step. This recovery step represents an advantage over the phosphine synthetic method, since it is not clear that nucleoside 3'-methylphosphine chlorides can be recovered after reaction.

As will be evident from the foregoing, two types of methylphosphonate oligomers were prepared in Example 1: those which contain only methylphosphonate linkages (oligomers 1-6) and those which terminate with a 5'-nucleoside 3'-p-chlorophenyl phosphotriester moiety (oligomers 7-10). Oligomers were synthesized on both 1% and 2% crosslinked supports. As shown in Table I, the average yield per coupling step which was determined by trityl group analysis was approximately 82%, for both types of support. This yield is adequate to allow preparation of protected octamers or nonamers in 25% and 20% overall yield, respectively.

Previous work has shown that methylphosphonate linkages are cleaved by base. It has been found this hydrolysis reaction depends to some extent upon the nucleoside sequence of the oligomer. Hydrolysis of methylphosphonate linkages by concentrated ammonium hydroxide in pyridine (1:1, v/v), the reagent commonly used to remove oligonucleotide base protecting groups, can be largely suppressed if the reactions are run at 0° C. However, these conditions are unsatisfactory for removal of oligonucleoside methylphosphonates from the polystyrene support.

Recently Barnett and Letsinger (Tetrahedron Letters 22; 991-994 (1981)) described removal of base protecting groups from oligonucleotide β,β,β-trichloroethyl-phosphotriesters using a mixture of ethylenediamine in phenol. According to the present invention, it has been found that ethylenediamine in ethanol (preferably 1:1, v/v) rapidly and cleanly removes benzoyl and isobutyryl protecting group from dA, dC and dG nucleosides. This reagent is particularly attractive since it can be easily removed by evaporation.

Oligonucleoside methylphosphonate can be cleaved from the support and base protecting groups removed by treatment with ethylenediamine/ethanol (1:1, v/v) at 65° C. for 3 hrs. It apears that the methylphosphonate linkages of at least some dimers are stable to these conditions. However, the linkages of longer oligomers appear to be hydrolyzed to various extents by this procedure at the indicated time and temperature conditions. This can result in loss of product as evidenced by the presence of shorter oligomers in amounts greater than might be expected based upon the coupling yields. To avoid this potential problem, it is preferred to carry out the deprotection reactions at lower temperatures and it has been found that these can be run effectively at room temperature (20–25° C.). Table II shows the half-lives for removing the base protecting groups from nucleosides at room temperature. While the isobutryl protecting group is removed at the slowest rate, all the groups are completely removed within 240 min. The sole product of each reaction is the 5′-O-dimethoxytritylnucleoside as shown by TLC.

It is also noted that the 5′-terminal nucleotide may be removed enzymatically to give an oligomer which contains only methylphosphonate linkages. Thus treatment of the nonamer, d-ApApApApGpCpApApG, with spleen phosphodiesterase gave d-Ap and the octamer d-ApApApGpCpApApG whose retention time is 16.4 min on the reversed phase column. The noncharged octamer was freed of d-Ap and enzyme by simply passing it through a small DEAE cellulose column.

Methylphosphonate linkages can be cleaved by base and according to the invention, it has been found that piperidine is particularly effective for this purpose. The cleavage occurs in a random manner giving nucleosides, nucleoside 3′- or 5′-methylphosphonates and nucleoside 3′-,5′-bis-methylphosphonates. This hydrolysis reaction may be used to characterize dimers, since the identity and ratio of the products formed are easily determined by reversed phase HPLC. However, the method becomes less satisfactory for longer oligomers.

Purine-containing oligonucleoside methylphosphonates may be depurinated by treatment by hydrochloric acid at 65° C. The methylphosphonate linkage is resistant to hydrolysis by these conditions as shown by the stability of d-TpT and d-TpTpT. On the other hand, dimers or trimers containing purine bases such as d-ApA, dApT, dTpA or d-ApApA have half-lives between 92 and 144 min in 0.01 M hydrochloric acid. Following neutralization with ammonium hydroxide, the products of these reactions were characterized by reversed phase HPLC. d-ApA gave adenine, while both d-ApT and d-TpA gave adenine and thymidine as the sole products of the reaction. Adenine and d-ApA were the only products observed when d-ApApA was partially hydrolyzed. When d-CpCpApT was completely hydrolyzed in acid three products, d-CpC, adenine and thymidine, were observed in a molar ratio of 1:1:1.

In contrast to the base hydrolysis of the methylphosphonate group, apurinic sites produced by acid treatment are further hydrolyzed to nucleosides or oligomers with free 5′- and 3′- OH groups. The absence of terminal phosphonate residues suggests hydrolysis occurs as shown in FIG. 3. The OH group on the 4′-carbon generated by opening the ribose at the apurinic site may participate in an intramolecular attack on the adjacent phosphonate linkages which results in removal of the phosphonate residues from the neighboring nucleoside hydroxyls.

Previous studies by others have indicated dithymidine methyl- or phenylphosphonates can be phosphorylated by polynucleotide kinase. Sinha et al supra reported that dimers but not trimers or tetramers served as substrates for this enzyme. It was not possible to phosphorylate tetramers or longer oligomers which contain only methylphosphonate linkages. However, those oligomers which terminate with a 5′-dAp-residue are readily phosphorylated by polynucleotide kinase. The phosphorylation reaction is easily followed by PEI-cellulose TLC. As shown in FIG. 4a, the phosphorylated oligomers have a higher Rf values than does ATP.

The phosphorylated methylphosphonate oligomers can be separated according to their chain lengths by polyacrylamide gel electrophoresis on an 18% gel containing 7 M urea as shown in FIG. 4(b). Lane 1 shows the separation of a trimer, hexamer and nonamer. The band which appears directly below the nonamer may arise from traces of contaminating octamer which were not removed during the purification of d-ApApApApGpCpApApG.

When the oligomers were partially hydrolyzed with piperidine, a series of new bands appears corresponding to shorter oligomers produced via hydrolysis of the methylphosphonate linkages (Lanes 2–4). Because of the random nature of this cleavage reaction, the oligomers should terminate with either a 3′-OH or a 3′-methylphosphonate group. In the case of the trimer, $^{32}$pApApA, hydrolysis gives two bands which correspond to d-$^{32}$pApA and d-$^{32}$pApAp (Lane 2). The same products are observed for hydrolysis of the nonamer, d-$^{32}$pApApApApGpCpApApG (Lane 4). A similar situation is observed for d$^3$pApGpCpApApG although the dimers d-$^{32}$pApG and d-$^{32}$pApGp have somewhat different mobilities (Lane 3). These dimers cannot be separated when the gel is run in the absence of urea.

It is possible to determine the chain lengths of the original oligomers by counting the number of oligomers produced by partial piperidine hydrolysis. For example, starting with the trimer band, one can observe 3 bands corresponding to tetramer, pentamer and hexamer for the hydrolysis products of d-$^{32}$pApGpCpApApG (Lane 3) and 6 bands corresponding to tetramer, pentamer, hexamer, heptamer, octamer and nonamer for the hydrolysis products of $^{32}$pApApApApGpCpApApG (Lane 4). The positions of the oligomers of the same chain length appear to be very similar which suggests that the mobilities are not greatly affected by base composition on the urea-containing gel. This procedure thus provides a rapid and convenient method for characterizing the methylphosphonate oligomers.

Treatment of the phosphorylated oligomers with acid produces shorter oligomers which result from chain cleavage at apurinic sites. In this case the oligomers terminate with a 3′-OH group. Treatment of $^{32}$pApGpCpApApG produces an intense band corresponding to the pentamer, d-$^{32}$pApGpCpApA (Lane 5) while treatment of $^{32}$pApApApApGpCpApApG produces an intense band corresponding to the octamer d-$^{32}$pApApApApGpCpApA and fainter bands corresponding to the heptamer, hexamer, tetramer and trimer. These results indicate that under the conditions used, hydrolysis occurs preferentially at the 3′-terminal G residue of both oligomers. It should be possible to extend this methodology to other base specific depurination or depyrimidination reactions similar to those employed in the Maxam-Gilbert sequencing method.

It will be appreciated that modifications may be made in various aspects of the invention without departing from the scope and essence thereof. Thus, it is evident that any suitable nucleoside or oligonucleoside bound to an appropriate polymer, preferably polystyrene, which is at least partially crosslinked, may be used for present purposes. Such nucleosides are commercially available or readily prepared by conventional or known means, and may be selected to provide the desired oligonucleoside sequence.

Likewise, any protected nucleoside or oligonucleoside alkyl or arylphosphonate may be employed. While the invention has been illustrated using the methylphosphonates, other alkyl or arylphosphonates, e.g. the phenyl, ethyl, propyl, or butylphosphonates or the like, may be used. Preferably the reactant is in the form of a methylphosphonate lower alkylamine, e.g. the triethylamine salt, but other equivalent materials may be used. The essential feature is to select a protected nucleoside alkyl or arylphosphonate for use with the polymer supported nucleoside, which will give the desired oligomer sequence.

In the examples given above, the protected nucleosides d-[(MeO)$_2$Tr]N and 5-dimethoxytrityl nucleosides esterified to 1% to 2% crosslinked polystyrene were obtained from commercial sources. The protected nucleoside 3'-methylphosphonate triethylammonium salts, d-[(MeO)$_2$Tr]Np.Et$_3$NH, was prepared in known manner.

The nucleoside loading level was 40 to 120 mol of nucleoside/g of support. Mesitylenesulfonyl-3-nitrotriazole (MSNT) was also obtained commercially while the anhydrous pyridine was prepared by refluxing previously purified pyridine over calcium hydride chips for several hours followed by distillation onto calcium hydride chips in 5 ml V-vials fitted with Teflon-lined septum caps. Lyophilized spleen phosphodiesterase, T-4 polynucleotide kinase and [μ-$^{32}$P]-ATP were obtained commercially. Reversed phase high performance liquid chromatography (HPLC) was carried out on Whatman Inc. C-18 (ODS-3) columns (0.4×25 cm). Analytical columns were eluted with 50 ml linear gradients of acetonitrile in water or acetonitrile in 0.1 M ammonium acetate (pH 5.8) at a flow rate of 2.5 ml/min. The eluate was monitored at 254 nm. The following molar extinction coefficients were used at 254 nm: d-T 7,250, dA 13,270, dC 6,260, dG 13,700. Unless otherwise noted, all reactions and operations were carried out at room temperature.

The specific conditions, e.g. time and temperature, selected for the condensation reaction and for separating the nucleotide from the polymer support and for removal of protecting groups can be widely varied. The essential point in selecting such conditions is to avoid undesired hydrolysis or side reactions which will reduce the yield of the desired oligonucleoside methylphosphonate.

It will be appreciated from the foregoing that the invention contemplates the condensation of protected nucleoside 3'-methylphosphonate triethylammonium salts with nucleosides or oligomers linked to a polystyrene support to obtain oligomers of desired length and sequence. The method involved is easy to use and allows relatively rapid synthesis of oligomers of defined sequence up to nine nucleosides in length or even more. Conditions for the efficient removal of base protecting groups and subsequent purification of the oligomers are also disclosed. Additionally contemplated are novel hydrolysis reactions which can be used as a basis for characterizing and sequencing these oligonucleotide analogs including, for example, hydrolysis at apurinic sites created by acid treatment of the oligomers.

While the accompanying drawings have been referred to above, the substance thereof is summarized below for convenience:

FIG. 1 shows the preparation of protected oligonucleoside methylphosphonates on a polystyrene support.

FIG. 2 comprises the reverse phase HLPC profile obtained in the purification of d-ApApApApGpCpApApG as follows: (a) oligomers obtained after treatment of support with ethylenediamine/ethanol (1:1, v/v). (b) oligomers obtained after treatment of the mixture in (1) with 80% acetic acid. (c) oligomers eluted from DEAE cellulose column with 0.15 M triethylammonium bicarbonate. (d) nonamer obtained after preparative reversed phase HPLC. Peaks marked with the symbol (X) are derived from impurities in the solvent used to elute the oligomer from the polystyrene support.

Figure 1:
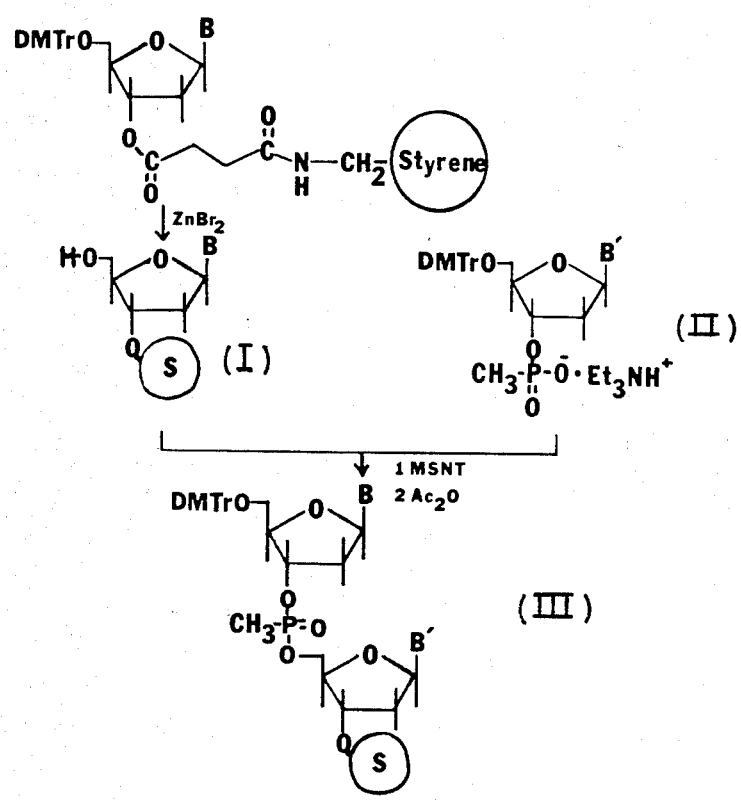
Figure 2:
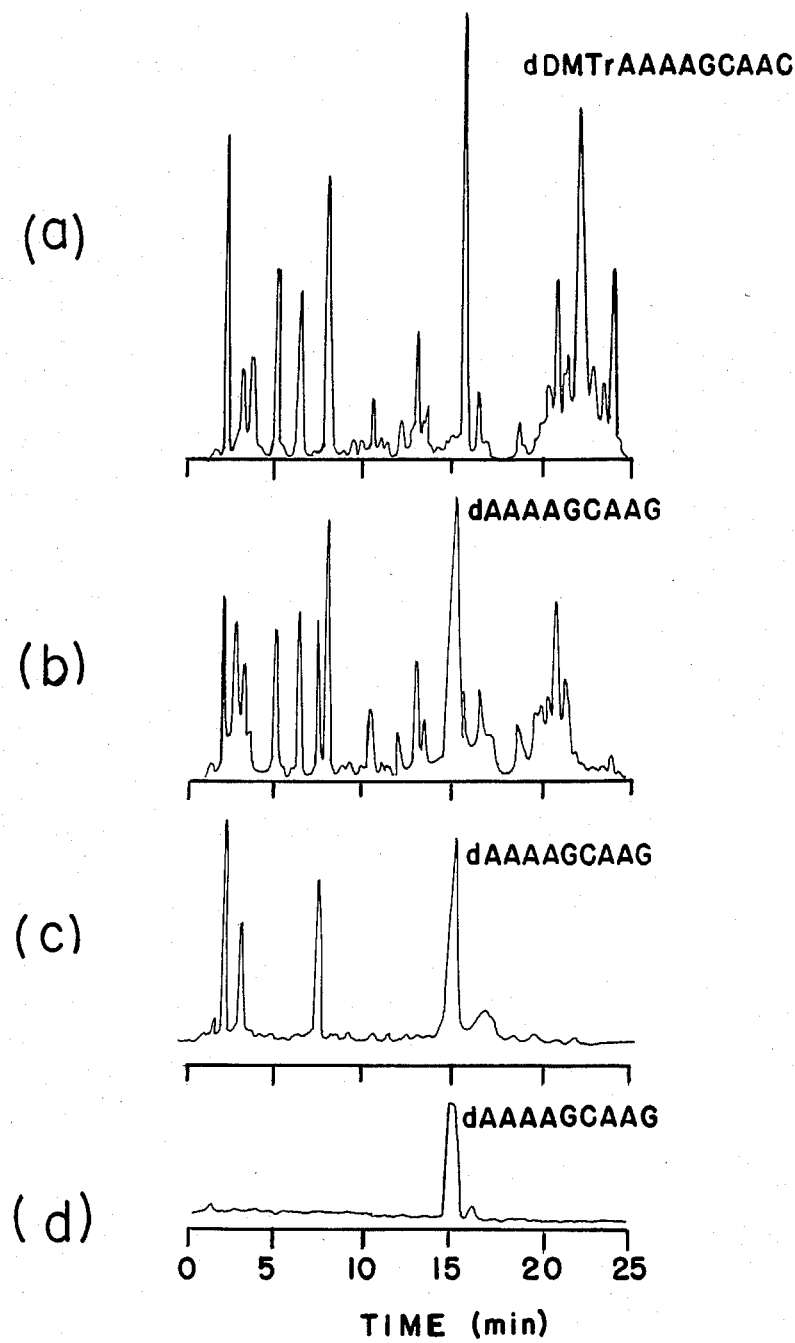
Figure 3:
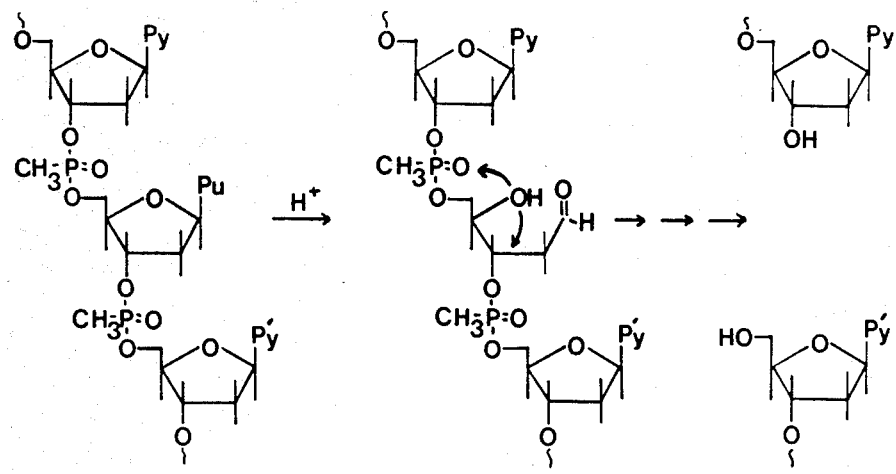
FIG. 3 illustrates the hydrolysis of the internucleoside methylphosphonate linkages at an apurinic site produced by treatment of the oligomer with hydrochloric acid at pH 2.
Figure 4:
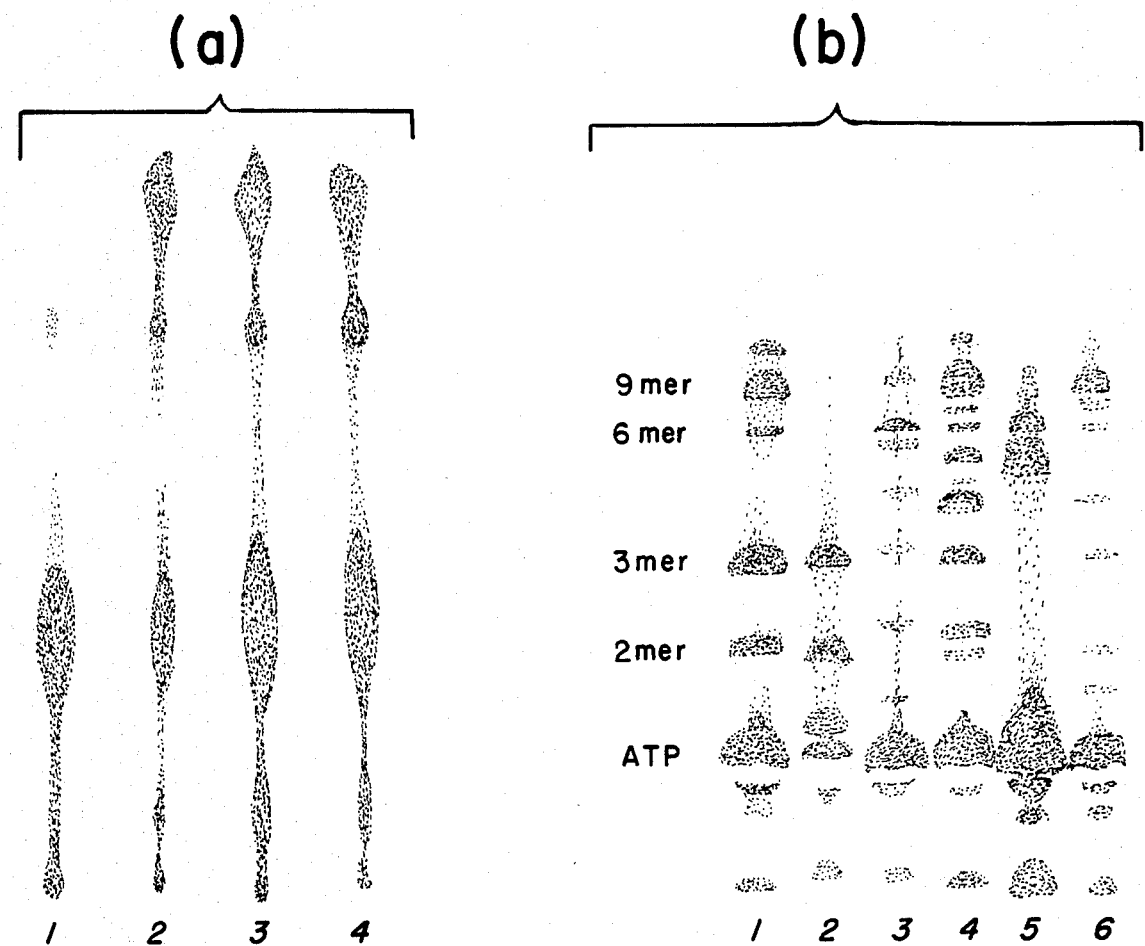
FIG. 4(a) shows the results obtained with PEI-cellulose TLC of T4 polynucleotide kinase reactions for: (1) [γ-$^{32}$p]ATP; (2) d-ApApA reaction mixture; (3) d-ApGpCpApApG reaction mixture; (4) d-ApApApApGpCpApApG reaction mixture. The chromatogram was eluted with 1.5 M pyridinium formate, pH 3.5.

FIG. 4(b) shows the results obtained with polyacrylamide gel electrophoresis of phosphorylated oligonucleoside methylphosphonates as follows: (1) markers: d-$^{32}$pTpT (2 mer); d-$^{32}$pApApA (3 mer); d-$^{32}$pApGpCpApApG (6 mer); d-$^{32}$pApApApApGpCpApApG (9 mer). Lanes 2–4: products obtained after partial hydrolysis of d$^{32}$pApApA (2); d-$^{32}$pApGpCpApApG (3) and d-$^{32}$pApApApApGpCpApApG; (4) with 0.5 M piperidine at 37° C. for 10 min. Lanes 5–6: products obtained after partial hydrolysis of d-$^{32}$p-ApGpCpApApG (5) and d-$^{32}$p-ApApApApGpCpApApG (6) with 0.5 M HCl at 37° for 30 min. Electrophoresis was carried out at constant voltage (800 v) until the bromphenol blue marker dye had migrated halfway down the gel.

The scope of the invention is defined in the following claims wherein:

We claim:

1. A process for synthesizing oligonucleoside alkyl or arylphosphonates which comprises condensing (1) a 5'-protected nucleoside 3'-alkyl or arylphosphonate alkylammonium salt with (2) a 5'-hydroxy nucleoside or oligomer thereof attached through its 3' position to a polymer support whereby condensation takes place between the 5'-hydroxy group of (2) and the alkylammonium group of (1), repeating said condensation if and as appropriate to obtain the oligonucleoside alkyl or aryl phosphonate of desired length attached to the support and then cleaving the oligomer product from the support by treating the same with a diamino alkane whereby the oligomer is cleaved from the support and base protecting groups are removed without hydrolysis of phosphonate linkages.

2. The process of claim 1 wherein the polymer is polystyrene and the protected nucleoside 3'-alkyl or arylphosphonate is a protected nucleoside 3'-methylphosphonate.

3. The process of claim 2 wherein the polystyrene is crosslinked.

4. The process of claim 3 wherein the protected nucleoside is a protected nucleoside 3'-methylphosphonate triethylammonium salt.

5. The process of claim 1 wherein the diamino alkane is ethylene diamine dissolved in ethanol.

6. The process of claim 5 wherein the treatment is carried out at room temperature.

7. The process of claim 1 wherein the support is dried before the condensation.

8. The process of claim 7 wherein the drying of the support is carried out by coevaporation with anhydrous pyridine.

9. The process of claim 1 wherein the synthesized oligomer contains only alkyl or arylphosphonate linkages.

10. The process of claim 9 wherein the synthesized oligomer is purified by reversed phase chromatography.

11. The process of claim 1 wherein the synthesized oligomer is terminated with a 5'-nucleotide residue.

12. The process of claim 11 wherein the synthesized oligomer is purified by ion exchange chromatography and reversed phase chromatography.

13. The process of claim 11 wherein the oligomer is phosphorylated by polynucleotide kinase and is separated by polyacrylamide gel electrophoresis.

14. The process of claim 1 including treatment of the synthesized oligomer with piperidine so as to cleave the oligomer methylphosphonate linkages.

15. The process of claim 1 wherein the synthesized oligomer is treated with acid to form apurinic sites which are spontaneously hydrolyzed to give oligomers which terminate with free 3' and 5' OH groups.

* * * * *